(12) United States Patent
Beck et al.

(10) Patent No.: US 6,576,582 B1
(45) Date of Patent: *Jun. 10, 2003

(54) BINDERLESS EX SITU SELECTIVATED ZEOLITE CATALYST

(75) Inventors: Jeffrey S. Beck, Lawrenceville; Jane C. Cheng, Clarksburg, both of NJ (US); Sharon B. McCullen, Newtown, PA (US); David H. Olson, Pennington; David L. Stern, Lawrenceville, both of NJ (US)

(73) Assignee: ExxonMobil Oil Corporation, Fairfax, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/558,309

(22) Filed: Nov. 15, 1995

Related U.S. Application Data

(60) Continuation-in-part of application No. 08/453,042, filed on May 30, 1995, now Pat. No. 5,633,417, which is a division of application No. 08/069,251, filed on May 28, 1993, now Pat. No. 5,476,823, application No. 08/558,309, which is a continuation-in-part of application No. 08/338,297, filed on Nov. 24, 1994, now Pat. No. 5,495,059, which is a division of application No. 08/069,255, filed on May 28, 1993, now Pat. No. 5,403,800.

(51) Int. Cl.[7] .............................. B01J 29/06; B01J 29/40
(52) U.S. Cl. .............................. 502/71; 502/63; 502/64; 502/77; 502/85
(58) Field of Search .............................. 502/63, 64, 71, 502/77, 85

(56) References Cited

U.S. PATENT DOCUMENTS

| | | |
|---|---|---|
| 3,251,897 A | 5/1966 | Wise |
| 3,257,310 A | 6/1966 | Plank et al. |
| 3,437,587 A | 4/1969 | Elbert et al. |
| 3,682,996 A | 8/1972 | Kerr |
| 3,698,157 A | 10/1972 | Allen et al. |
| 4,016,218 A | 4/1977 | Haag et al. |
| 4,049,738 A | 9/1977 | Young |
| 4,060,568 A | 11/1977 | Rodewald |
| 4,086,287 A | 4/1978 | Kaeding et al. |
| 4,090,981 A | 5/1978 | Rodewald |
| 4,100,215 A | 7/1978 | Chen |
| 4,117,024 A | 9/1978 | Kaeding |
| 4,127,616 A | 11/1978 | Rodewald |
| 4,145,315 A | 3/1979 | Rodewald |
| 4,224,141 A | 9/1980 | Morrison et al. |
| 4,283,306 A | 8/1981 | Herkes |
| 4,326,994 A | 4/1982 | Haag et al. |
| 4,402,867 A | 9/1983 | Rodewald |
| 4,443,554 A | 4/1984 | Dessau |
| 4,465,886 A | 8/1984 | Rodewald |
| 4,477,583 A | 10/1984 | Rodewald |
| 4,487,843 A | 12/1984 | Telford et al. |
| 4,522,929 A | 6/1985 | Chester et al. |
| 4,548,914 A | 10/1985 | Chu |
| 4,559,314 A | 12/1985 | Shihabi |
| 4,582,815 A | 4/1986 | Bowes |
| 4,843,057 A | 6/1989 | D'Amore et al. |
| 4,851,604 A | 7/1989 | Absil et al. |
| 4,927,979 A | 5/1990 | Yamagishi et al. |
| 4,950,835 A | 8/1990 | Wang et al. |
| 5,173,461 A | 12/1992 | Absil et al. |
| 5,403,800 A * | 4/1995 | Beck et al. .................... 502/64 |
| 5,476,823 A * | 12/1995 | Beck et al. .................... 502/60 |

FOREIGN PATENT DOCUMENTS

EP  296 582 A2  6/1988

OTHER PUBLICATIONS

Nakajima et al., "p–Xylene–Selective Disproportionation of Toluene over a Modified Pentasil Type Zeolite", *Sekiyu Gakkaishi*, 35(2), 185–189 (1992).
Hibino et al., "Shape–Selectivity over HZSM–5 Modified by Chemical Vapor Deposition of Silicon Alkoxide ", *Journal of Catalysis*, 128, 551–558 (1991).
Lago et al., "The Nature of the Catalytic Sites in HZSM–5 Activity Enhancement", *New Development in Zeolite Science Technology: Proceeding of the 7th International Zeolite Conference*, 677–684 (1986).

* cited by examiner

*Primary Examiner*—Steven Bos
*Assistant Examiner*—Christina Ildebrando

(57) ABSTRACT

There is provided a substantially binder-free catalytic molecular sieve which has been modified by being ex situ selectivated with a silicon compound. The ex situ selectivation involves exposing the molecular sieve to at least two silicon impregnation sequences, each sequence comprising an impregnation with a silicon compound followed by calcination. The catalyst may be used in a hydrocarbon conversion process, such as toluene disproportionation.

12 Claims, No Drawings

US 6,576,582 B1

BINDERLESS EX SITU SELECTIVATED ZEOLITE CATALYST

CROSS-REFERENCE TO RELATED APPLICATION

This application is a continuation-in-part of U.S. application Ser. No. 08/453,042, filed May 30, 1995, now U.S. Pat. No. 5,633,417, which, in turn, is a division of U.S. application Ser. No. 08/069,251, filed May 28, 1993, now U.S. Pat. No. 5,476,823 the entire disclosure of which is incorporated herein by reference.

This application is also a continuation-in-part of U.S. application Ser. No. 08/338,297, now U.S. Pat. No. 5,495,059, filed Nov. 24, 1994, which, in turn, is a division of U.S. application Ser. No. 08/069,255, filed May 28, 1993, now U.S. Pat. No. 5,403,800, the entire disclosure of which is incorporated herein by reference.

BACKGROUND OF THE INVENTION

The present invention is directed to a selectivated binder-free catalytic molecular sieve.

The term "shape-selective catalysis" describes catalytic selectivities in zeolites. The principles behind shape selective catalysis have been reviewed extensively, e.g., by N. Y. Chen, W. E. Garwood, and F. G. Dwyer, *Shape Selective Catalysis in Industrial Applications*, 36, Marcel Dekker, Inc. (1989). Within a zeolite pore, hydrocarbon conversion reactions such as paraffin isomerization, olefin skeletal or double bond isomerization, oligomerization and aromatic disproportionation, alkylation or transalkylation reactions are governed by constraints imposed by the channel size. Reactant selectivity occurs when a fraction of the feedstock is too large to enter the zeolite pores to react; while product selectivity occurs when some of the products cannot leave the zeolite channels. Product distributions can also be altered by transition state selectivity in which certain reactions cannot occur because the reaction transition state is too large to form within the zeolite pores or cages. Another type of selectivity results from configurational constraints on diffusion where the dimensions of the molecule approach that of the zeolite pore system. A small change in the dimensions of the molecule or the zeolite pore can result in large diffusion changes leading to different product distributions. This type of shape selective catalysis is demonstrated, for example, in selective toluene disproportionation to para-xylene.

The production of para-xylene is typically performed by methylation of toluene or by toluene disproportionation over a catalyst under conversion conditions. Examples include the reaction of toluene with methanol as described by Chen et al., *J. Amer. Chem. Soc.* 101, 6783 (1979), and toluene disproportionation, as described by Pines in *The Chemistry of Catalytic Hydrocarbon Conversions*, Academic Press, NY, 72 (1981). Such methods typically result in the production of a mixture including para-xylene, ortho-xylene, and meta-xylene. Depending upon the degree of selectivity of the catalyst for para-xylene (para-selectivity) and the reaction conditions, different percentages of para-xylene are obtained. The yield, i.e., the amount of xylene produced as a proportion of the feedstock, is also affected by the catalyst and the reaction conditions.

Various methods are known in the art for increasing the para-selectivity of zeolite catalysts. One such method is to modify the catalyst by treatment with a "selectivating agent". For example, U.S. Pat. 5,173,461; 4,950,835; 4,927,979; 4,465,886; 4,477,583; 4,379,761; 4,145,315; 4,127,616; 4,100,215; 4,090,981; 4,060,568; and 3,698,157 disclose specific methods for contacting a catalyst with a selectivating agent containing silicon ("silicon compound").

U.S. Pat. No. 4,548,914 describes another modification method involving impregnating catalysts with oxides that are difficult to reduce, such as those of magnesium, calcium, and/or phosphorus, followed by treatment with water vapor to improve para-selectivity.

European Patent No. 296,582 describes the modification of aluminosilicate catalysts by impregnating such catalysts with phosphorus-containing compounds and further modifying these catalysts by incorporating metals such as manganese, cobalt, silicon and Group IIA elements. The patent also describes the modification of zeolites with silicon compounds.

Traditionally, ex situ pre-selectivation of zeolites has involved single applications of the selectivating agent. It may be noted, however, that the suggestion of multiple treatments was made in U.S. Pat. No. 4,283,306 to Herkes. The Herkes patent discloses the promotion of crystalline silica catalyst by application of an amorphous silica such as ethylorthosilicate. The Herkes patent contrasts the performance of catalyst treated once with an ethylorthosilicate solution followed by calcination against the performance of catalyst treated twice with ethylorthosilicate and calcined after each treatment. The Herkes disclosure, however, shows that the twice-treated catalyst is less active and less selective than the once-treated catalyst as measured by methylation of toluene by methanol. Thus, Herkes indicates that multiple ex situ selectivation confers no benefit and in fact reduces a catalyst's efficacy in shape-selective reactions.

In U.S. Pat. Ser. No. 08/269,051, the first multiple ex situ selectivation sequence of catalytic molecular sieves to enhance selectivity in hydrocarbon conversion reactions was described. These catalysts proved particularly useful in toluene disproportionation as demonstrated in U.S. Pat. Nos. 5,365,004 and 5,367,099 which issued on the 15th and 22nd of November 1994, respectively. The disclosures of U.S. Pat. Nos. 5,365,004 and 5,367,099 are herein incorporated by reference.

However, because the para-isomers of alkyl-substituted aromatic hydrocarbons (e.g., para-xylene) are utilized to produce a variety of commercial products, there is still a continuing need in the art to increase the efficiency of production.

Accordingly, it is an object of the present invention to improve the efficiency of producing alkyl-substituted aromatic hydrocarbons utilizing ex situ selectivated catalytic molecular sieves.

SUMMARY OF THE INVENTION

There is provided a method for preparing a catalyst, said method comprising the steps of:

(a) contacting a substantially binder-free catalytic molecular sieve under liquid phase conditions with an organosilicon selectivating agent under conditions sufficient to impregnate said molecular sieve with said organosilicon selectivating agent;

(b) calcining the impregnated molecular sieve of step (a) under conditions sufficient to decompose said organosilicon selectivating agent and leave a siliceous residue of said agent on said molecular sieve; and (c) repeating steps (a) and (b) at least once.

There is also provided a method for preparing a catalyst, said method comprising the steps of:

(a) mulling and then extruding a mixture comprising water, ZSM-5, sodium ions and no intentionally added binder material under conditions sufficient to form an extrudate having an intermediate green strength sufficient to resist attrition during ion exchange step (b) set forth hereinafter;

(b) contacting the uncalcined extrudate of step (a) with an aqueous solution comprising ammonium cations under conditions sufficient to exchange cations in said ZSM-5 with ammonium cations;

(c) calcining the ammonium exchanged extrudate of step (b) under conditions sufficient to generate the hydrogen form of said ZSM-5 and increase the crush strength of said extrudate;

(d) contacting the substantially binder-free ZSM-5 extrudate of step (c) under liquid phase conditions with an organosilicon selectivating agent under conditions sufficient to impregnate said extrudate with said organosilicon selectivating agent;

(e) calcining the impregnated molecular sieve of step (d) under conditions sufficient to decompose said organosilicon selectivating agent and leave a siliceous residue of said agent on said molecular sieve; and (f) repeating steps (d) and (e) at least once.

There is also provided a process for hydrocarbon conversions, such as toluene disproportionation reactions, using this catalyst.

Shape selective hydrocarbon conversions over the present modified catalytic molecular sieve may be conducted by contacting a reaction stream comprising an alkyl-substituted aromatic hydrocarbon, under conversion conditions, with the present modified catalytic molecular sieve. The modified catalytic molecular sieve is a substantially binder-free catalytic molecular sieve which had been exposed, preferably, to at least two ex situ selectivation sequences. Each ex situ selectivation sequence includes impregnating the substantially binder-free catalytic molecular sieve with a selectivating agent, followed by calcination after each impregnation. Selectivating agents useful in the present invention include a large variety of silicon-containing compounds, preferably silicon polymers soluble in organic carriers. Such organic carriers include various alkanes, preferably paraffins having 6 or more carbons.

The alkyl substituted aromatic hydrocarbon is preferably an alkyl-substituted benzene, such as ethylbenzene or toluene.

The modified catalytic molecular sieve may be further modified by in situ trim-selectivating the modified catalytic molecular sieve. The in situ trim-selectivation may be performed by coke trim-selectivation wherein an organic compound is decomposed in the presence of the modified catalytic molecular sieve, at conditions suitable for decomposing the organic compound. Alternatively, the trim-selectivation may be performed by exposing the modified catalytic molecular sieve to a reaction stream that includes a hydrocarbon to be converted and a trim-selectivating agent selected from a group of compounds including a large variety of silicon-containing compounds, at reaction conditions.

Advantageously, these modified catalysts have enhanced shape selectivity in the production of alkylaromatic hydrocarbons. The catalysts also provide the advantage of exhibiting enhanced selectivity at lower operating temperatures, which in turn lengthens the effective life cycle of the catalysts. Accordingly, the shape selective hydrocarbon process of the invention exhibits increased selectivity, especially in the production of para-xylene.

DETAILED DESCRIPTION

It has now been found by utilizing multiple ex situ selectivated catalytic molecular sieves that are substantially binder-free, enhanced selectivity for the para-isomer of the converted hydrocarbon can now be obtained at lower operating temperatures in comparison to catalytic molecular sieves that have been incorporated into a binder.

By reference to "substantially binder-free catalytic molecular sieves" it is meant to include catalytic molecular sieves (or zeolites) that are binderless or unbound, i.e., have not been incorporated into a binder material. However, this phrase does exclude catalytic molecular sieves which may contain trace amounts of binder material as an impurity. Impurities can be inadvertently introduced during the manufacturing process, for example by utilizing equipment that had been previously used to manufacture bound catalysts. Another source of impurities can be non-zeolite material during processing of the unbound catalysts. This can be due to partial dissolution of the zeolite during aqueous treatment, extrusion with or without extrusion aids (e.g., caustics, burnout materials, etc.), steaming and other processes.

The binder-free molecular sieve is preferably in the form of an extrudate. Methods for preparing such binder-free extrudates are described in U.S. Pat. Nos. 4,582,815 and 4,872,968. A particular method for preparing such a binder-free extrudate may involve the steps of:

(a) mulling and then extruding a mixture comprising water, ZSM-5, sodium ions and no intentionally added binder material under conditions sufficient to form an extrudate having an intermediate green strength sufficient to resist attrition during ion exchange step (b) set forth hereinafter;

(b) contacting the uncalcined extrudate of step (a) with an aqueous solution comprising ammonium cations under conditions sufficient to exchange cations in said ZSM-5 with ammonium cations;

(c) calcining the ammonium exchanged extrudate of step (b) under conditions sufficient to generate the hydrogen form of said ZSM-5 and increase the crush strength of said extrudate.

The ability to operate the catalysts at a lower operating temperature provides many advantages which will be apparent to the skilled artisan. First, the reduction in operating temperature lengthens the cycle life of the catalysts. Thus, the catalysts can remain on-stream longer and require regeneration less often. This in turn makes utilizing the catalysts more economical in the sense that there is less down time in the hydrocarbon conversion operation.

The lower operating temperatures also make the catalysts well suited for high conversion processes since the catalysts of the present invention will run at lower temperatures in comparison to the bound counterparts. Thus, in high conversion processes where it may not have been practical to run bound multiple ex situ selectivated catalysts, the unbound catalysts of the present invention provide the skilled artisan a new alternative. By reference to high conversion processes, hydrocarbon conversion reactions at a conversion level of 35 wt. % or greater are contemplated. It is particularly contemplated that the present catalysts could be utilized in hydrocarbon conversion reactions up to 50 wt. % hydrocarbon conversion due to their lower operating temperature requirements. The ability to run these catalysts at such high conversion levels would allow their use as a possible substitute catalyst in the Tatoray process, which is widely utilized for toluene production.

According to an embodiment of the present method, a zeolite in unbound form is impregnated preferably at least twice, and more preferably between about two and about six times, with a selectivating agent. The selectivating agent comprises a compound or polymer containing a silicon. In order to facilitate a more controlled application of the selectivating agent, the selectivating agent can be dispersed in a liquid carrier, more particularly an aqueous or an organic liquid carrier.

In each phase of the selectivation treatment, the selectivating agent is deposited on the external surface of the catalyst by any suitable method. For example, a selectivating agent may be dissolved in a carrier, mixed with the catalyst, and then dried by evaporation or vacuum distillation. This method is termed "impregnation". The molecular sieve may be contacted with the silicon compound at a molecular sieve/silicon compound weight ratio of from about 100/1 to about 1/100.

The silicon compound employed may be in the form of a solution or an emulsion under the conditions of contact with a zeolite. It is believed that the deposited silicon compound extensively covers, and resides substantially exclusively on, the external surface of the molecular sieve. Examples of methods of depositing silicon on the surface of the zeolite are found in U.S. application Ser. No. 08/069,251, filed May 28, 1993, and in U.S. Pat. No. 5,403,800, which are incorporated by reference herein.

As was described above, the catalysts useful in the present invention are ex situ selectivated by multiple coatings with a selectivating agent, each coating followed by calcination and optional trim-selectivation with additional selectivating agent. The term "para-selectivating agent" or "selectivating agent" is used herein to indicate substances which will increase the shape-selectivity of a catalytic molecular sieve to the desired levels in hydrocarbon conversion reactions, such as toluene disproportionation, while maintaining commercially acceptable levels of toluene to xylene conversion. Such substances include, for example, organic silicon compounds such as phenylmethyl silicone, dimethyl silicone, and blends thereof which have been found to be suitable.

Useful selectivating agents include siloxanes which can be characterized by the general formula:

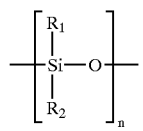

where $R_1$ is hydrogen, halogen, hydroxyl, alkyl, halogenated alkyl, aryl, halogenated aryl, aralkyl, halogenated aralkyl, alkaryl or halogenated alkaryl. The hydrocarbon substituents generally contain from 1 to 10 carbon atoms, preferably methyl, ethyl or phenyl groups. $R_2$ is independently selected from the same group as $R_1$, and n is an integer of at least 2 and generally in the range of 3 to 1000. The molecular weight of the silicone compound employed is generally between about 80 and about 20,000 and preferably within the approximate range of 150 to 10,000. Representative silicone compounds include dimethyl silicone, diethyl silicone, phenylmethyl silicone, methylhydrogen silicone, ethylhydrogen silicone, phenylhydrogen silicone, methylethyl silicone, phenylethyl silicone, diphenyl silicone, methyltrifluoropropyl silicone, ethyltrifluoropropyl silicone, polydimethyl silicone, tetrachlorophenylmethyl silicone, tetrachlorophenylethyl silicone, tetrachlorophenylhydrogen silicone, tetrachlorophenylphenyl silicone, methylvinyl silicone and ethylvinyl silicone. The silicone compound need not be linear, but may be cyclic, for example, hexamethyl cyclotrisiloxane, octamethyl cyclotetrasiloxane, hexaphenyl cyclotrisiloxane and octaphenyl cyclotetrasiloxane. Mixtures of these compounds may also be used, as may silicones with other functional groups.

Preferred silicon-containing selectivating agents include dimethylphenylmethyl polysiloxane (e.g., Dow-550) and phenylmethyl polysiloxane (e.g., Dow-710). Dow-550 and Dow-710 are available from Dow Chemical Co., Midland, Mi.

Preferably, the kinetic diameter of the high efficiency, p-xylene selectivating agent is larger than the zeolite pore diameter, in order to avoid entry of the selectivating agent into the pore and any concomitant reduction in the internal activity of the catalyst.

Examples of suitable carriers for the selectivating silicon compound include linear, branched, and cyclic alkanes having five or more carbons. In the methods of the present invention it is preferred that the carrier be a linear, branched, or cyclic alkane having a boiling point greater than about 70° C., and most preferably containing 6 or more carbons. Optionally, mixtures of low volatility organic compounds, such as hydrocracker recycle oil, may be employed as carriers. Particular low volatility hydrocarbon carriers of selectivating agents are decane and dodecane.

It has also been found that a multiple selectivation scheme provides unexpectedly increased efficiency of deposition of the silicon compound on the surface of the catalyst. This increased efficiency allows for the use of relatively small quantities of the silicon compound as well as relatively small quantities of the carrier. A more detailed discussion on the increased efficacy of depositing silicon compounds via multiple ex situ selectivation is described in U.S. Ser. No. 08/069,251 filed May 28, 1993, as well as in U.S. Pat. No. 5,403,800.

Following each deposition of the silicon compound, the catalyst is calcined to decompose the molecular or polymeric species to a solid state species. The catalyst may be calcined at a rate of from about 0.2° C./minute to about 5° C./minute to a temperature greater than 200° C., but below a temperature at which the crystallinity of the zeolite is adversely affected. Generally, such temperature will be below 600° C. Preferably the temperature of calcination is within the approximate range of 350° C. to 550° C. The product is maintained at the calcination temperature usually for 1 to 24 hours, preferably for between 2 and 6 hours.

The catalyst may be calcined in an atmosphere of $N_2$, an oxygen-containing atmosphere, preferably air, an atmosphere of $N_2$ followed by an oxygen-containing atmosphere, or an atmosphere containing a mixture of $N_2$ and air. Calcination should be performed in an atmosphere substantially free of water vapor, to avoid undesirable uncontrolled steaming of the silicon coated catalyst. The catalyst may be calcined once or more than once after each silicon deposition. The various calcinations in any impregnation sequence need not be identical, but may vary with respect to the temperature, the rate of temperature rise, the atmosphere and the duration of calcination.

Factors upon which the amount of silica incorporated with the zeolite is dependent include temperature, concentration of the silicon compound in the containing medium (the carrier material), the degree to which the zeolite has been dried prior to contact with the silicon compound, and calcination of the zeolite.

After the selectivation sequence, the catalyst may be subjected to steam treatment at a temperature of from about 100° C. to about 600° C., preferably from about 175° C. to about 325° C.; with from about 1% to about 100% steam, preferably from about 50% to about 100% steam; at a pressure of from about 0.01 psia to about 50 psia; for about two to about twelve hours, preferably from about three to about six hours. The selectivated molecular sieve catalyst can show improved selectivity upon steaming. Excessive steaming, however, can be detrimental to a selectivated catalyst.

The alkylaromatic may be fed simultaneously with a second selectivating agent and hydrogen at reaction conditions until the desired shape-selectivity is attained, whereupon the co-feed of selectivating agent is discontinued. This co-feeding of selectivating agent with alkylaromatic is one type of "trim-selectivation" . Reaction conditions for this in situ trim-selectivation step generally include a temperature of from about 350° C. to about 540° C. and a pressure of from about atmospheric to about 5000 psig. The reaction stream is fed to the system at a rate of from about 0.1 WHSV to about 20 WHSV. Hydrogen may be fed at a hydrogen to hydrocarbon molar ratio of from about 0.1 to about 20.

The selectivating agent for trim-selectivation may comprise a silicon compound discussed in greater detail above. For example, organic silicon compounds such as phenylmethyl silicone, dimethyl silicone, and mixtures thereof are suitable. According to one embodiment of the present invention, a silicone containing phenylmethylsilicone and dimethylsilicone groups in a ratio of about 1:1 is co-fed to the system, while the other components, e.g., alkylbenzene and hydrogen, are fed in the amounts set forth above. The para-selectivating agent is fed in an amount of from about 0.001 wt. % to about 10 wt. % of the alkylaromatic according to this preferred embodiment. Depending upon the percentage of selectivating agent used, the trim-selectivation will last for at least one hour, preferably about 1 to about 48 hours, most preferably less than 24 hrs.

In this scheme the silicon compound will decompose to deposit additional silica to on the catalyst. During the selectivation procedure the para-selectivity of the catalyst will be observed to increase further. The silicon containing polymer or molecular species may be dissolved in toluene or another appropriate hydrocarbon carrier.

Alternatively, the catalyst, prior to contacting with alkylaromatic under conversion conditions, may be subjected to trim-selectivation with a thermally decomposable organic compound at an elevated temperature in excess of the decomposition temperature of said compound but below the temperature at which crystallinity of the zeolite is adversely affected. Generally, this temperature will be less than about 650° C.

Organic materials, thermally decomposable under the above temperature conditions to provide coke trimming, encompass a wide variety of compounds including by way of example, hydrocarbons, such as paraffinic, cycloparaffinic, olefinic, cycloolefinic and aromatic; oxygen-containing organic compounds such as alcohols, aldehydes, ethers, ketones and phenols; heterocyclics such as furans, thiophenes, pyrroles and pyridines. Usually, it is contemplated that a thermally decomposable hydrocarbon, such as an alkyl-substituted aromatic, will be the source of coke, most preferably the alkylaromatic being subjected to the conversion process itself. In the latter case, the alkylaromatic is initially brought into contact with the catalyst under conditions of temperature and hydrogen concentration amenable to rapid coke formation. Typically, coke trimming is conducted at conditions outside the operating parameters used during the main time span of the catalytic cycle. When the desired coke deposition has been effected, the alkylaromatic feed is continued in contact with the coke-containing catalyst under conditions of temperature and hydrogen concentration conducive to hydrocarbon conversion process, with a greatly reduced coking rate. While not wishing to be bound by theory, it is believed that the advantages of the present invention are in part obtained by rendering acid sites on the external surfaces of the catalyst substantially inaccessible to reactants, while increasing catalyst tortuosity. Acid sites existing on the external surface of the catalyst are believed to isomerize the solution-phase para-isomer back to an equilibrium level with the other two isomers. In the case of xylene production, for example, the amount of p-xylene in the xylenes is reduced to about 24%, equilibrium selectivity. By reducing the availability of these acid sites to the solution-phase p-xylene, the relatively high proportion of p-xylene can be maintained. It is believed that the para-selectivating agents of the present invention block or otherwise render these external acid sites unavailable to the para-isomer by chemically modifying said sites.

The catalytic molecular sieves useful in accordance with the methods of the present invention are preferably in the hydrogen form prior to modification, but may be in the ammonium or sodium form. Preferably, the catalytic molecular sieve comprises an intermediate pore-size zeolite such as a ZSM-5, ZSM-11, ZSM-22, ZSM-23, or ZSM-35 as discussed above. The catalytic molecular sieves, prior to selectivation, also preferably have a Constraint Index of about 1–12. The details of the method by which Constraint Index is determined are described fully in U.S. Pat. No. 4,016,218, incorporated herein by reference.

As previously described, the catalytic molecular sieves useful herein have a Constraint Index from about 1 to about 12 which includes intermediate pore zeolites. Zeolites which conform to the specified values of constraint index for intermediate pore zeolites include ZSM-5, ZSM-11, ZSM-5/ZSM-11intermediate, ZSM-12, ZSM-22, ZSM-23, ZSM-35, ZSM-48, ZSM-50, and ZSM-57. Such zeolites are described, for example, in U.S. Pat. Nos. 3,702,886 and Re. No. 29,949; 3,709,979; 3,832,449; 4,046,859; 4,556,447; 4,076,842; 4,016,245; 4,229,424; 4,397,827; 4,640,849; 4,046,685; 3,308,069 and Re. 28,341, to which reference is made for the details of these zeolites.

The crystal size of zeolites used herein is preferably greater than 0.1 micron, e.g., from 0.1 to 1 micron, e.g., from 0.1 to 0.5 micron. The accurate measurement of crystal size of zeolite materials is frequently very difficult. Microscopy methods, such SEM and TEM, are often used, but these methods require measurements on a large number of crystals and for each crystal measured, values may be required in up to three dimensions. For ZSM-5 materials described in the examples below, estimates were made of the effective average crystal size by measuring the rate of sorption of 2,2-dimethylbutane at 90° C. and 60 torr hydrocarbon pressure. The crystal size is computed by applying the diffusion equation given by J. Crank, *The Mathematics of Diffusion*, Oxford at the Clarendon Press, 52–56 (1957), for the rate of sorbate uptake by a solid whose diffusion properties can be approximated by a plane sheet model. In addition, the diffusion constant of 2,2-dimethylbutane, D, under these conditions is taken to be $1.5 \times 10^{-14}$ cm$^2$/sec. The relation between crystal size measured in microns, d, and diffusion time measured in minutes, $t_{0.3}$. the time required for the uptake of 30% of capacity of hydrocarbon, is:

$$d = 0.0704 \times t_{0.3}^{1/2}.$$

In the present case these measurements have been made on a computer controlled, thermogravimetric electrobalance, but there are numerous ways one skilled in the art could obtain the data. The larger crystal material used herein has a sorption time, $t_{0.3}$, of 497 minutes, which gives a calculated crystal size of 1.6 microns. The smaller crystal material has a sorption time of 7.8 minutes, and a calculated crystal size of 0.20 micron.

The "alpha value" of a catalyst is an approximate indication of the catalytic cracking activity of the catalyst compared to a standard catalyst, and it gives the relative rate constant (rate of normal hexane conversion per volume of catalyst per unit time). It is based on the activity of the amorphous silica-alumina cracking catalyst taken as an alpha of 1 (Rate Constant=0.016 sec$^{-1}$). The alpha test is described in U.S. Pat. No. 3,354,078 and in *The Journal of Catalysis*, 4, 522–529 (1965); 6, 278 (1966); and 61, 395 (1980), each incorporated herein by reference as to that description. It is noted that intrinsic rate constants for many acid-catalyzed reactions are proportional to the alpha value for a particular crystalline silicate catalyst (see "The Active Site of Acidic Aluminosilicate Catalysts," *Nature*, 309, No. 5959, 589–591 (1984). The experimental conditions of the test used herein include a constant temperature of 538° C. and a variable flow rate as described in detail in the *Journal of Catalysis*, 61, 395 (1980). The catalyst in the present invention preferably has an alpha value greater than 1, for example, from about 1 to about 2000. The alpha value of the catalyst may be increased by initially treating the catalyst with nitric acid or by mild steaming before pre-selectivation. This type of steaming is discussed in U.S. Pat. No. 4,326,994.

The silica to alumina ratio of the catalysts of the invention may be determined by conventional analysis. This ratio is meant to represent, as closely as possible, the ratio in the rigid atomic framework of the zeolite crystal and to exclude aluminum in the binder or in cationic or other form within the channels. The silica to alumina molar ratio of the present zeolites may be less than 60, e.g., from 20 to 40.

Production of Dialkyl-Substituted Benzenes

The modified zeolite catalysts are advantageously used in the conversion of alkylbenzene compounds to provide dialkyl-substituted benzene products which are highly enriched in the para-dialkyl substituted benzene isomer. Examples of alkylbenzenes to be utilized include ethylbenzene and toluene, toluene being more preferred. Conversion reactions of this type include alkylation, transalkylation and disproportionation. Alkylations of reactions in which the catalysts of the invention can be used are described, for example, in U.S. Pat. Nos. 3,755,483, 4,086,287, 4,117,024 and 4,117,026, which are incorporated herein by reference.

As described in U.S. Pat. No. 3,755,483 to Burress, aromatic hydrocarbons such as benzenes, naphthalenes, anthracenes and substituted derivatives thereof, e.g., toluene and xylene, may be alkylated with alkylating agents such as olefins ethylene, propylene, dodecylene, and formaldehyde, alkyl halides, and alkyl alcohols with 1 to 24 carbons under vapor phase conditions including a reactor inlet temperature up to about 482° C., with a reactor bed temperature up to about 566° C., at a pressure of about atmospheric to about 3000 psia, a mole ratio of aromatic/alkylating agent of from about 1:1 to about 20:1, and a WHSV of 20 to 3000 over ZSM-12.

As described in U.S. Pat. No. 4,086,287 to Kaeding et al., monoalkylbenzenes having alkyls of 1–2 carbons, such as toluene and ethylbenzene, may be ethylated to produce a para-ethyl derivative, e.g., para-ethyltoluene at a temperature of from about 250° C. to about 600° C., a pressure of 0.1 atmospheres to 100 atmospheres, a weight hourly space velocity (WHSV) of 0.1 to 100, and a ratio of feed/ethylating agent of 1 to 10 over a catalyst having an acid activity, i.e., alpha, of 2 to 5000, modified by pre-coking or combining with oxides of phosphorus, boron or antimony to attain a catalyst with a xylene sorption capacity greater than 1 g/100 g of zeolite and an ortho xylene sorption time for 30% of said capacity of greater than 10 minutes, where sorption capacity and sorption time are measured at 120° C. and a xylene pressure of 4.5±0.8 mm of mercury.

U.S. Pat. No. 4,117,024 to Kaeding describes a process for the ethylation of toluene or ethylbenzene to produce p-ethyltoluene at a temperature of 350° C. to 550° C., a critical pressure of greater than one atmosphere and less than 400 psia, with hydrogen/ethylene ratio of 0.5 to 10 to reduce aging of the catalyst. The zeolite described in U.S. Pat. No. 4,117,024 has a crystal size greater than one micron, and is modified as the catalyst in U.S. Pat. No. 4,086,287 to attain the sorption capacity described in U.S. Pat. No. 4,086,287.

U.S. Pat. No. 4,117,026 to Haag and Olson describes the production of para-dialkyl benzenes having alkyls of 1 to 4 carbons under conditions which vary according to the feed. When the feed includes monoalkyl-substituted benzenes having an alkyl group of 1 to 4 carbons, olefins of 2 to 15 carbons, or paraffins of 3 to 60 carbons or mixtures thereof, conversion conditions include a temperature of 250° C. to 750° C., a pressure of 0.1 to 100 atmospheres and a WHSV of 0.1 to 2000. For the disproportionation of toluene, the conditions include a temperature of 400° C. to 700° C., a pressure of 1 to 100 atmospheres and a WHSV of 1–50. When the feed includes olefins of 2 to 15 carbons including cyclic olefins, the conversion conditions include a temperature of 300° C. to 700° C., a pressure of 1 to 100 atmospheres and a WHSV of 1 to 1000. When the feed includes paraffins of 3 to 60 carbons, conditions include a temperature of 300° C. to 700° C., a pressure of 1 to 100 atmospheres and a WHSV of 0.1 to 100. However for lower paraffins of 3 to 5 carbons, the temperature should be above 400° C. When the feed includes mixed aromatics such as ethylbenzene and toluene, and also optionally olefins of 2 to 20 carbons or paraffins of 5 to 25 carbons, conversion conditions include a temperature of 250° C. to 500° C. and a pressure greater than 200 psia. In the absence of added aromatics, the olefins and higher paraffins are more reactive and require lower severity of operation, e.g., a temperature of 250° C. to 600° C., preferably 300° C. to 550° C.

In general, therefore, catalytic conversion conditions over a catalyst comprising the modified zeolite include a temperature of from about 100° C. to about 760° C., a pressure of from about 0.1 atmosphere (bar) to about 200 atmospheres (bar), a weight hourly space velocity of from about 0.08 to about 2000, and a hydrogen/organic, e.g., hydrocarbon compound, mole ratio of from 0 to about 100.

Toluene Disproportionation

Alkyl-substituted benzenes, such as toluene and ethylbenzene, may be disproportionated over a multiply-selectivated catalyst. Normally a single pass conversion of an alkylbenzene stream results in a product stream which includes dialkylbenzenes having alkyl groups at all locations, i.e., o-, m-, and p-dialkylbenzenes. A catalyst treated in the manner described herein exhibits a desirable decreased ortho-dialkylbenzene sorption rate parameter and yields a significantly para-selected product from alkylbenzene disproportionation. For example, diffusion rate constants in toluene disproportionation have been discussed by D. H. Olson and W. O. Haag, "Structure-Selectivity Relationship in Xylene Isomerization and Selective Toluene Disproportionation", *Catalytic Materials: Relationship Between Structure and Reactivity*, ACS Symposium Ser. No. 248 (1984).

In toluene disproportionation, toluene diffuses into the zeolite with a diffusivity $D_T$. The toluene undergoes disproportionation to p-, m-, and o-xylene and benzene at a total rate constant $k_D$. For high selectivity and catalyst efficiency it is desirable to have $$k_D << \frac{D_T}{r^2}.$$

The degree of para-selectivity depends on the activity and the diffusion characteristics of the catalyst. The primary product will be rich in the para isomer if initially produced m- and o-xylene diffuse out of the zeolite crystal at a rate $(D_{m,o}/r^2)$ that is lower than that of their conversion to p-xylene $(k_I)$, as well as lower than that of the p-xylene diffusion $(D_p/r^2)$ out of the catalyst, where:

$D_m$=diffusion of m-xylene;
$D_o$=diffusion of o-xylene;
$D_p$=diffusion of p-xylene;
r=length of diffusion path (crystal size);
$k_I$=rate of interconversion via isomerization of xylene isomers yielding secondary xylene product m-xylene and o-xylene.

It is desirable to increase the para-selectivity of the catalyst. Practically, this involves decreasing the o- and m-xylene diffusivities such that $$k_r > \frac{D_{m,o}}{r^2}.$$

In such a case the rate of conversion of m- and o-xylenes to p-xylene exceeds the diffusivities of the m- and o-xylenes. As a result, the proportion of the xylene yield that is p-xylene will be increased. Those skilled in the art will appreciate that similar considerations apply to the diffusivities of other alkylbenzenes.

Near regioselective conversion of toluene to para-xylene may be achieved by disproportionating toluene in a reaction stream containing a toluene feed with a selectivated and optionally steamed catalytic molecular sieve in the presence of hydrogen and at reaction conditions suitable to provide p-xylene selectivity of greater than about 80%, even greater than 90%.

As will be apparent to one skilled in the art, with an increase in conversion comes a decrease in regioselectivity for the para-isomer. However, the decrease in regioselectivity will still remain above the equilibrium level for the para-isomer, in the case of para-xylene above 24 wt. % regioselectivity.

The production stream will also contain small amounts of o- and m-xylene and trace amounts of impurities such as ethylbenzene. The amount of these non-desired products will become greater as the conversion level of disproportionation reaction increases.

As used herein, the term "para-xylene selectivity" means the proportion of p-xylene, indicated as a percentage, among all of the xylene products, i.e., p-xylene, o-xylene, and m-xylene. Those skilled in the art will appreciate that the relative proximity of the boiling points of these xylene isomers necessitates relatively expensive separation processes for the isolation of p-xylene. On the other hand, p-xylene is more readily separated from other components in the product stream such as benzene, toluene, and p-ethyltoluene.

As explained in greater detail herein, the presently modified catalyst may be used in a process for obtaining p-xylene at toluene conversions of at least 10%, preferably at least about 15–35%, with a p-xylene selectivity of greater than 80%, e.g., at least 85%. As stated previously, in high conversion processes where toluene conversion exceeds 35% the p-xylene selectivity will decrease but still remain above equilibrium levels, i.e., 24% para-selectivity. For example, one skilled in the art can expect that the para-selectivity to decrease to as low as 50% when toluene conversion levels are pushed to 45%–50%.

The present toluene disproportionation product may comprise at least 80 wt % of paraxylene, based on the total xylene isomers in the product, while at the same time producing at least 14.2 wt %, e.g., at least 14.5 wt %, of paraxylene, based on the total weight of hydrocarbons in the product.

The toluene feedstock preferably includes about 50% to 100% toluene, more preferably at least about 80% toluene. Other compounds such as benzene, xylenes, and trimethylbenzene may also be present in the toluene feedstock without adversely affecting the disproportionation product.

The toluene feedstock may also be dried, if desired, in a manner which will minimize moisture entering the reaction zone. Numerous methods known in the art are suitable for drying the toluene charge for the process of the invention. These methods include percolation through any suitable desiccant, for example, silica gel, activated alumina, molecular sieves or other suitable substances, or the use of liquid charge dryers.

Operating conditions employed in the process of the present invention will affect the para-selectivity and toluene conversion. Such conditions include the temperature, pressure, space velocity, molar ratio of the reactants, and the hydrogen to hydrocarbon mole ratio ($H_2$/HC). It has also been observed that an increased space velocity (WHSV) can enhance the para-selectivity of the modified catalyst in alkylbenzene disproportionation reactions. This characteristic of the modified catalyst allows for substantially improved throughput when compared to current commercial practices. In addition, it has been observed that the disproportionation process may be performed using $H_2$ as a diluent, thereby dramatically increasing the cycle length of the catalyst.

A selectivated catalytic molecular sieve may be contacted with a toluene feedstock under conditions for effecting vapor-phase disproportionation. Conditions effective for accomplishing the high para-selectivity and acceptable toluene disproportionation conversion levels include a reactor inlet temperature of from about 200° C. to about 600° C., preferably from 350° C. to about 540° C.; a pressure of from about atmospheric to about 5000 psia, preferably from about 100 to about 1000 psia; a WHSV of from about 0.1 to about 20, preferably from about 2 to about 10; and a $H_2$/HC mole ratio of from about 0.1 to about 20, preferably from about 2 to about 6. This process may be conducted in either batch or fluid bed operation, with the attendant benefits of either operation readily obtainable. The effluent may be separated and distilled to remove the desired product, i.e., p-xylene, as well as other by-products. Alternatively, the $C_8$ fraction may be subjected to further separation, as in the case of xylenes, subjected to crystallization or the PAREX process to yield p-xylene.

The catalyst may be further modified in order to reduce the amount of undesirable by-products, particularly ethylbenzene. The state of the art is such that the reactor effluent from standard toluene disproportionation typically contains about 0.5% ethylbenzene by-product. Upon distillation of the reaction products, the level of ethylbenzene in the $C_8$ fraction often increases to between about 3% and 4%. This level of ethylbenzene is unacceptable for polymer grade p-xylene, since ethylbenzene in the p-xylene product., if not removed, degrades the quality of fibers ultimately produced from the p-xylene product. Consequently, ethylbenzene content of the p-xylene product must be kept low. The specification for the allowable amount of ethylbenzene in the p-xylene product has been determined by the industry to be less than 0.3%. Ethylbenzene can be substantially removed by crystallization, by selective sorption or by superfractionation processes.

In order to avoid the need for downstream ethylbenzene removal, the level of ethylbenzene by-product is advantageously reduced by incorporating a hydrogenation/ dehydrogenation function within the catalyst, such as by addition of a metal compound such as platinum. While platinum is the preferred metal, other metals of Groups IB to VIII of the Periodic Table such as palladium, nickel, copper, cobalt, molybdenum, rhodium, ruthenium, silver, gold, mercury, osmium, iron, zinc, cadmium, and mixtures thereof, may be utilized. The metal may be added by cation exchange, in amounts of from about 0.001% to about 2%, typically about 0.5%. For example, a platinum modified catalyst can be prepared by first adding the catalyst to a solution of ammonium nitrate in order to convert the catalyst to the ammonium form. The catalyst is subsequently contacted with an aqueous solution of tetraamine platinum(II) nitrate or tetraamine platinum(II) chloride. The catalyst can then be filtered, washed with water and calcined at temperatures of from about 250° C. to about 500° C. It will be appreciated by those skilled in the art that similar considerations apply to processes involving alkylbenzenes other than toluene.

EXAMPLES

The following non-limiting Examples illustrate the invention in relation to the disproportionation of toluene as well as in relation to the similar disproportionation of ethylbenzene.

In the Examples, the o-xylene sorption rate parameter $D_o/r^2$ was measured at 120° C. and 3.8 torr.

$D_o$=diffusivity of o-xylene r=crystal size $D_o/r^2$=the diffusion rate parameter is a measure of the speed of movement of o-xylene into and out of the catalyst crystals

Example 1

A four-times selectivated bound catalyst (4× bound) was prepared by contacting a batch of H-ZSM-5/SiO$_2$ (65% H-ZSM-5A/35% SiO$_2$) with a 7.8 wt. % solution of dimethylphenylmethyl polysiloxane (Dow-550) in decane. Subsequently, the decane was stripped off the catalyst. The catalyst was then calcined in a muffle furnace under N$_2$, followed by air. The temperature of the furnace was elevated gradually at 2° C./min. until 538° C. and maintained at that temperature. This procedure was repeated an additional three times to obtain a catalyst that was four-times selectivated.

Example 2

A five-times selectivated bound catalyst (5× bound) was prepared by contacting a batch of H-ZSM-5/SiO$_2$ (65% H-ZSM-5A/35% SiO$_2$) with a 7.8 wt. % solution of Dow-550 in decane and subsequently calcined following the procedure described in Example 1. This was then repeated an additional three times. Thereafter, the catalyst was then contacted with a 2 wt. % solution of Dow-550 in decane and subsequently calcined to obtain a five-times selectivated bound catalyst.

Example 3

A four-times selectivated unbound catalyst (4× unbound) was prepared by contacting a batch of H-ZSM-5 with a 9 wt. % solution of Dow-550 in decane and subsequently calcining the catalyst utilizing the procedure described in Example 1. This procedure was repeated for an additional three times to obtained a four-times selectivated unbound catalyst.

Comparative Toluene Disproportionation Runs

Example 4

Toluene Disproportionation runs utilizing the catalysts prepared in Example 1–3 were conducted with an automated unit. The unit has an automated sampling feature with on-line gas chromatography (GC) for characterization of the entire product effluent. Approximately one gram of the 4× bound catalyst, 5× bound catalyst and 4× unbound catalyst were individually loaded into 0.25 diameter, stainless steel tube reactors and then placed into the automated unit. The catalysts was then heated to reaction temperature under N$_2$.

Each catalytic run was initiated with a pure toluene feed at 282 psig, a H$_2$/HC ratio of 1, and a weight hourly space velocity of 3. The temperature of each run was varied to obtain a toluene conversion level of approximately 30%. Samples of the reactor effluent were taken and analyzed. The product composition of these samples as ascertained by GC analysis and the reaction conditions at the time these samples were taken are shown in Table 1.

TABLE 1

| Conditions | 4× Bound | 5× Bound | 4× Unbound |
|---|---|---|---|
| Temperature (° C.) | 401 | 410 | 387 |
| Pressure (psig) | 282 | 282 | 274 |
| H$_2$/HC | 1 | 1 | 1 |
| WHSV (1/H) | 3 | 3 | 3 |
| Products | | | |
| C$_5$— | 0.9 | 1.1 | 1.0 |
| Benzene | 13.1 | 14.2 | 13.8 |
| Ethylbenzene | 0.4 | 0.4 | 0.4 |
| Xylenes | 14.9 | 13.8 | 14.4 |
| Para-xylene | 12.3 | 13.0 | 13.4 |
| Toluene conversion (%) | 30.0 | 30.1 | 30.1 |
| Para-selectivity (%) | 82.9 | 94.4 | 93.0 |
| Benzene/Xylene (Molar) | 1.2 | 1.4 | 1.3 |

The advantages in utilizing unbound multiply selectivated catalysts are apparent from Table 1. The 4× unbound catalyst, surprisingly, exhibited a 10.1% increase in para-selectivity over its 4× bound counterpart (93.0% versus 82.9%). This increased para-selectivity exhibited by the 4× unbound catalyst is in fact comparable to para-selectivity exhibited by the 5× bound catalyst (93.0% versus 94.4%).

The 4× unbound catalyst, moreover, exhibited a lower operating temperature. The operating temperature 4× unbound catalyst was 14° C. less than the operating temperature its bound counterpart and 23° F. less than the operating temperature of the 5× bound catalyst (387° C. versus 401° C. & 410° C.). As will be apparent to the skilled artisan, this lower operating temperature requirement will enable the unbound catalyst to run longer on-stream since the catalysts will require regeneration less frequently than their bound counterparts.

Example 5

To observe the reduced operating temperature requirement of the 4× unbound catalyst at a higher toluene conversion level, the WHSV was reduced from 3 to 1 to increase the level of conversion. A sample of the reactor effluent was subjected to GC analysis. The product composition of this sample and the reaction conditions are shown in Table 2.

TABLE 2

| Conditions | 4× Unbound |
|---|---|
| Temperature (° C.) | 375 |
| Pressure (psig) | 274 |
| $H_2$/HC | 1 |
| WHSV (1/H) | 1 |
| Products | |
| $C_{5-}$ | 1.0 |
| Benzene | 15.6 |
| Ethylbenzene | 0.5 |
| Xylenes | 17.9 |
| Para-xylene | 14.8 |
| Toluene conversion (%) | 36.1 |
| Para-selectivity (%) | 82.0 |
| Benzene/Xylene (Molar) | 1.2 |

At a conversion level of 36.1%, the unbound catalyst still exhibited a para-selectivity of 82% and a reduced operating l:temperature of 375° C. Also noteworthy was that the total amount of para-xylene produced utilizing the 4× unbound catalyst at 36.1% conversion was, in fact, greater than the total amount of para-xylene produced in any of the disproportionation runs of Example 1 (14.8 wt. % versus 12.3 wt. %, 13.0 wt. % & 13.4 wt. %).

Accordingly, the unbound catalysts of the present invention offer distinct advantages over their bound counterparts, especially in terms of their reduced operating temperature requirements and high para-selectivity. These unique properties are not diminished, but in fact become more evident, as hydrocarbon conversion exceeds 35%. This was exemplified by the improved net production of para-xylene as the toluene conversion level of the 4× unbound catalyst was increased from 30.1% to 36.1%. Likewise, the lower operating temperature requirements of the unbound catalysts will increase the amount of time the catalysts can remain on-stream as compared to their bound counterparts, which in turn provides a distinct economic advantage in itself.

We claim:

1. A method for preparing a catalyst, said method comprising the steps of:
   (a) contacting a substantially binder-free catalytic molecular sieve under liquid phase conditions with an organosilicon selectivating agent under conditions sufficient to impregnate said molecular sieve with said organosilicon selectivating agent wherein said catalytic molecular sieve is a zeolite having a constraint index from about 1 to about 12;
   (b) calcining the impregnated molecular sieve of step (a) under conditions sufficient to decompose said organosilicon selectivating agent and leave a siliceous residue of said agent on said molecular sieve; and
   (c) repeating steps (a) and (b) at least once.

2. The method of claim 1, wherein said binder-free catalytic molecular sieve is in the form of an extrudate.

3. The method of claim 1, wherein steps (a) and (b) are repeated between one and five times.

4. The method of claim 1, wherein steps (a) and (b) are repeated three or four times.

5. The method of claim 1, wherein the selectivating agent is selected from the group consisting of silicones, silicone polymers, silanes, and alkoxysilanes.

6. The method of claim 1, wherein the selectivating agent comprises dimethylphenylmethyl polysiloxane.

7. The method of claim 1, wherein the selectivating agent is dispersed in an organic carrier.

8. The method of claim 7, wherein the organic carrier is a paraffin containing at least 6 carbon atoms.

9. The method of claim 1, wherein the catalytic molecular sieve comprises ZSM-5.

10. A method for preparing a catalyst, said method comprising the steps of:
    (a) mulling and then extruding a mixture comprising water, ZSM-5, sodium ions and no intentionally added binder material under conditions sufficient to form an extrudate having an intermediate green strength sufficient to resist attrition during ion exchange step (b) set forth hereinafter;
    (b) contacting the uncalcined extrudate of step (a) with an aqueous solution comprising ammonium cations under conditions sufficient to exchange cations in said ZSM-5 with ammonium cations;
    (c) calcining the ammonium exchanged extrudate of step (b) under conditions sufficient to generate the hydrogen form of said ZSM-5 and increase the crush strength of said extrudate;
    (d) contacting the substantially binder-free ZSM-5 extrudate of step (c) under liquid phase conditions with an organosilicon selectivating agent under conditions sufficient to impregnate said extrudate with said organosilicon selectivating agent;
    (e) calcining the impregnated molecular sieve of step (d) under conditions sufficient to decompose said organosilicon selectivating agent and leave a siliceous residue of said agent on said molecular sieve; and
    (f) repeating steps (d) and (e) at least once.

11. A method according to claim 10, wherein said ZSM-5 has a silica to alumina molar ratio of 60 or less.

12. A method according to claim 11, wherein said ZSM-5 has a silica to alumina molar ratio of from 20 to 40.

* * * * *